(12) United States Patent
Takehiro (10) Patent No.: US 11,619,630 B2
(45) Date of Patent: Apr. 4, 2023

(54) IMMUNOCHROMATOGRAPHY DEVICE (71) Applicant: SANWA KAGAKU KENKYUSHO CO., LTD., Nagoya (JP)

(72) Inventor: Osamu Takehiro, Inabe (JP)

(73) Assignee: SANWA KAGAKU KENKYUSHO CO., LTD., Nagoya (JP)

( * ) Notice: Subject to any disclaimer, the term of this patent is extended or adjusted under 35 U.S.C. 154(b) by 368 days.

(21) Appl. No.: 16/954,058

(22) PCT Filed: Dec. 21, 2018

(86) PCT No.: PCT/JP2018/047162
§ 371 (c)(1),
(2) Date: Jun. 16, 2020

(87) PCT Pub. No.: WO2019/124532
PCT Pub. Date: Jun. 27, 2019

(65) Prior Publication Data
US 2020/0333336 A1 Oct. 22, 2020

(30) Foreign Application Priority Data

Dec. 22, 2017 (JP) .............................. JP2017-246301

(51) Int. Cl.
G01N 33/543 (2006.01)
B01L 3/00 (2006.01)
G01N 33/58 (2006.01)

(52) U.S. Cl.
CPC ........ *G01N 33/54366* (2013.01); *B01L 3/508* (2013.01); *G01N 33/58* (2013.01);
(Continued)

(58) Field of Classification Search
CPC ............... B01L 3/508; B01L 2300/041; B01L 2300/0609; B01L 2300/0825;
(Continued)

(56) References Cited

U.S. PATENT DOCUMENTS 5,252,496 A   10/1993  Kang et al.
5,559,041 A    9/1996  Kang et al.
(Continued)

FOREIGN PATENT DOCUMENTS

JP   H04-289456 A   10/1992
JP   H09-184840 A    7/1997
(Continued)

OTHER PUBLICATIONS

Apr. 2, 2019 International Search Report issued in International Patent Application No. PCT/JP2018/047162.
(Continued)

*Primary Examiner* — Dennis White
(74) *Attorney, Agent, or Firm* — Oliff PLC (57) ABSTRACT A test strip including: a first site that's a detection site, where a first antibody specifically binding to the substance to be measured is immobilized on a porous carrier; a second site that's a specimen liquid addition site, where a second labeled antibody binding to the substance to be measured and having a recognition site different from that of the first antibody is retained on a porous carrier to be movable; and a third site that is a specimen liquid or developer addition site, where colored microparticles bound with a substance binding to a label substance of the second antibody are retained on a porous carrier to be movable, wherein the second site is provided between the first and the third sites, and the specimen liquid or developer can move, due to capillarity, from the second site to the first and from the third to the first site.

13 Claims, 2 Drawing Sheets

(52) U.S. Cl.
CPC . *B01L 2300/041* (2013.01); *B01L 2300/0609* (2013.01); *B01L 2300/0825* (2013.01); *G01N 2458/00* (2013.01)

(58) Field of Classification Search
CPC .......... B01L 2400/0406; B01L 3/5023; G01N 33/58; G01N 2458/00; G01N 33/54386; G01N 33/558
See application file for complete search history.

(56) References Cited

U.S. PATENT DOCUMENTS

| | | | |
|---|---|---|---|
| 5,728,587 | A | 3/1998 | Kang et al. |
| 6,027,943 | A | 2/2000 | Kang et al. |
| 6,221,625 | B1 | 4/2001 | Ashihara et al. |
| 6,737,277 | B1 | 5/2004 | Kang et al. |
| 7,270,995 | B2 | 9/2007 | Matsushita et al. |
| 9,562,908 | B2 | 2/2017 | Yoshida et al. |
| 2001/0005585 | A1 | 6/2001 | Ashihara et al. |
| 2002/0160525 | A1 | 10/2002 | Kang et al. |
| 2003/0143639 | A1 | 7/2003 | Matsushita et al. |
| 2008/0145835 | A1 | 6/2008 | Alajem et al. |
| 2012/0225496 | A1 | 9/2012 | Yoshida |
| 2015/0111307 | A1 | 4/2015 | Yoshida et al. |
| 2015/0285799 | A1 | 10/2015 | Esfandiari |
| 2016/0038935 | A1* | 2/2016 | Alajem .................. B01L 3/5023 422/420 |
| 2017/0212108 | A1 | 7/2017 | Li et al. |
| 2018/0292398 | A1 | 10/2018 | Wada et al. |

FOREIGN PATENT DOCUMENTS

| | | |
|---|---|---|
| JP | H10-68730 A | 3/1998 |
| JP | H10-177028 A | 6/1998 |
| JP | H10-300750 A | 11/1998 |
| JP | 2001-337091 A | 12/2001 |
| JP | 2003-344413 A | 12/2003 |
| JP | 2008-286590 A | 11/2008 |
| JP | 2009-2822 A | 1/2009 |
| WO | 2011/062157 A1 | 5/2011 |
| WO | 2017/104143 A1 | 6/2017 |

OTHER PUBLICATIONS

Jan. 10, 2023 Office Action issued in Chinese Patent Application No. 201880080517.2.

* cited by examiner

IMMUNOCHROMATOGRAPHY DEVICE

TECHNICAL FIELD

The present invention relates to an immunochromatographic test strip, a cassette for housing the test strip, and an immunochromatographic apparatus in which the test strip is housed in the cassette.

BACKGROUND ART

In clinical tests and the like, immunoassay methods are used as methods for measuring components in a specimen. Among them, an immunochromatographic method is widely used in clinical sites and the like because of its simple operation and possible measurement in a short time. A general test strip for the immunochromatographic method is composed of a porous carrier called sample pad to which a specimen is to be added, a porous carrier called conjugate pad in which a colored microparticle-labeled antibody is dissolved in a specimen liquid and retained so as to be movable, a porous carrier called membrane in which an antibody is immobilized at a position of a detection line and the liquid having passed through and flowed out of the conjugate pad develops, and a water absorbing material called absorption pad that absorbs the liquid having developed in the membrane.

The measurement by a general immunochromatographic method is performed by adding a specimen to a sample pad. A substance to be measured and the colored microparticle-labeled antibody move on the membrane while forming a complex. When passing through the detection line, the complex is captured by the immobilized antibody. The captured complex is observed as a linearly developed color. This method is widely used in the inspection of infectious diseases. Generally, the result is determined to be positive when the developed color is confirmed and to be negative otherwise.

In the immunochromatographic method, the measurement sensitivity tends to increase as the reaction time is lengthened, but the reaction time problematically becomes longer accordingly, leading to a reduction in convenience. In recent years, studies on increasing the sensitivity of the immunochromatographic method have made it possible to make a positive determination in a shorter time and to detect a more trace amount of a substance to be measured.

As methods of increasing the color development of a detection line to increase the sensitivity, there are disclosed a method of adding a water-soluble polymer compound (Patent Literature 1), a method of sensitizing a colloidal metal as a label substance using a silver-containing compound and a reducing agent for silver ions (Patent Literature 2), and a method of using organic colored microparticles having an increased amount of the developed color (Patent Literature 3). However, in each case, there are problems that the reaction between the substance to be measured and the antibody is performed between the antibody bound to the colored microparticles, and, furthermore, that the reaction is performed while they move in the porous carrier of the membrane, and thus that the efficiency of the antigen-antibody reaction is low due to the dynamic constraint, steric hindrance and the like. Therefore, when it is necessary to measure a low concentration of a substance to be measured in order to improve the reaction efficiency, measures such as slowing down the developing speed of the specimen or developing a large amount of the specimen, for example, have been taken.

Further, as methods for improving the reaction efficiency to improve the sensitivity, a method of efficiently capturing a complex of a colored microparticle-labeled antibody and a substance to be measured on a detection line (Patent Literature 4) and a method of efficiently performing a binding reaction between a colored microparticle-labeled antibody and a substance to be measured (Patent Literature 5) are disclosed. It has been pointed out that, in measurement principle, the immunochromatographic method has a poor reaction efficiency between a substance to be measured and a colored microparticle-labeled antibody and a poor capturing efficiency on a detection line, for example, due to steric hindrance by the colored microparticle-labeled antibody. These disclosed methods have merely improved either one of the problems, and the problem still remains.

Furthermore, while the immunochromatographic measurement is generally completed by a one-step operation of adding a specimen or immersing an end of a test strip in a container containing the specimen, a method of performing measurement by a two-step operation of adding a buffer solution to another place after adding the specimen is disclosed. It has been shown that, by performing the operation in two steps, the effect of a reaction inhibitor contained in a specimen can be avoided (Patent Literatures 6 and 8). However, the operation becomes complicated, and, besides, the problem of the efficiency of capturing the colored microparticles on the detection line still remains. Furthermore, the implementation of enzyme immunoassay by an immunochromatographic method is indicated (Patent Literature 7), but, in addition to the problem of a complicated operation, a sufficient time is required for an enzymatic reaction, so that the measurement time problematically becomes longer.

Furthermore, for example, in the case of a commercially available kit for measuring infectious diseases such as influenza and adenovirus, when the concentration of the substance to be measured is high, the detection line can develop a color in a few minutes, so that the result can be determined to be positive. When the concentration of the substance to be measured is low, however, it takes time for the detection line to develop a color, and thus a measurement time of approximately 8 to 15 minutes is set. On the other hand, even after a lapse of the measurement time, the development of the specimen is continued, so that the reaction between a minor amount of the remaining colored microparticle-labeled antibodies and the substance to be measured gradually progresses. Therefore, if the reaction time is longer than necessary, false positive may appear. Therefore, in such a commercially available kit, attention is given not to perform measurement beyond the measurement time.

CITATIONS LIST

Patent Literature

Patent Literature 1: JP 2003-344413 A
Patent Literature 1: JP 2008-286590 A
Patent Literature e: WO 2011/062157
Patent Literature 1: JP H9-184840 A
Patent Literature 5: JP H10-68730 A
Patent Literature 6: JP 2001-337091 A
Patent Literature 7: JP H10-300750 A
Patent Literature 8: JP 2009-002822 A

SUMMARY OF INVENTION

Technical Problems

The problem to be solved by the present invention is to provide an immunochromatographic test strip which solves the problem of reaction efficiency in an immunochromatographic method and enables determination with high sensitivity in a short time by a simple operation, a cassette for housing the test strip, and an immunochromatographic apparatus in which the test strip is housed in the cassette.

Solutions to Problems

The present inventor has conducted intensive studies to solve the above problems, and, as a result, has found that it is difficult to improve the reaction efficiency by the conventional immunochromatographic method involving reacting a substance to be measured and a colored microparticle-labeled antibody while moving them on a membrane, and then capturing a conjugate of the colored microparticle-labeled antibody and the substance to be measured by an antibody immobilized on a detection line. So, when first performing the two-step antigen-antibody reaction, which has been conducted in the conventional immunochromatographic method, in the absence of the colored microparticle, and then performing measurement using a test strip configured so that the colored microparticle is captured by the conjugate of the substance to be measured and the antibody captured on the detection line, the present inventor has found that the measurement can be performed with high sensitivity in a short time. However, this test strip has a site that retains the antibody that is first reacted with the substance to be measured and a site that retains the colored microparticle, and a specimen liquid is added dropwise to the former and a specimen liquid or developer is added dropwise to the latter. That is, dropping must be performed twice, resulting in a more complicated operation than in the conventional method. Therefore, the present inventor has devised a cassette in which the specimen liquid can be introduced into the two sites of the test strip by a single dropping operation. Thus, the present inventor has created an immunochromatographic apparatus capable of performing measurement with high sensitivity in a short time without sacrificing the operability, and has completed the present invention.

Specifically, the present invention is as follows.

[1] A test strip for detecting a substance to be measured in a specimen liquid by an immunochromatographic method, the test strip having:
(1) a first site that is a detection site, where a first antibody specifically binding to the substance to be measured is immobilized on a porous carrier;
(2) a second site that is an addition site of the specimen liquid, where a second antibody that is a labeled antibody specifically binding to the substance to be measured and having a recognition site different from that of the first antibody is retained on a porous carrier so as to be movable; and
(3) a third site that is an addition site of the specimen liquid or a developer, where a colored microparticle bound with a substance specifically binding to the label substance of the second antibody are retained on a porous carrier so as to be movable,
wherein the second site is provided between the first site and the third site, and the specimen liquid or developer can move, due to capillarity, from the second site to the first site and from the third site to the first site.

[2] The test strip according to [1], further having a control line in the vicinity of the first site on the side opposite to the second site, the control line indicating that a reaction has been performed normally.

[3] The test strip according to [1] or [2], wherein, in the second site, compared to the addition site of the specimen liquid, a site containing the labeled second antibody is located closer to the first site.

[4] The test strip according to any one of [1] to [3], further having a water absorber or a porous carrier for absorbing or moving the specimen liquid or developer on the side of the first site and/or the control line, opposite to the second site.

[5] The test strip according to any one of [1] to [4], wherein the label substance of the second antibody is a biotin, and the substance specifically binding to the label substance of the second antibody, which is bound to the colored microparticle, is selected from the group consisting of streptavidin, neutravidin and an anti-biotin antibody.

[6] The test strip according to [5], wherein the streptavidin is a complex with a protein.

[7] The test strip according to any one of [1] to [6], wherein the colored microparticle is selected from the group consisting of a colloidal metal, a colored latex, and a colored cellulose particle.

[8] The test strip according to any one of [1] to [7], which is for use wherein the specimen liquid or developer is added to the second site and the third site simultaneously or to the third site subsequent to the second site.

[9] A cassette for housing a test strip for detecting a substance to be measured in a specimen liquid by an immunochromatographic method, having a determination window and a concave specimen addition section arranged on its upper surface,
the cassette having:
a convex part having a first through hole in the concave specimen addition section;
a second through hole on the side of the concave specimen addition section, opposite to the determination window; and
a groove formed in an area ranging from the concave specimen addition section to the second through hole, the groove having a flow path for sending a part of the added specimen liquid leaked from the first through hole of the convex part.

[10] The cassette according to [9], wherein the groove is provided with a porous carrier as the flow path for sending the liquid, and wherein one end of the porous carrier is provided so as to come into contact with the test strip housed in the cassette through the second through hole.

[11] The cassette according to [9] or [10], further having a lid attached to the groove.

[12] An immunochromatographic apparatus, in which the test strip according to any one of [1] to [8] is housed in the cassette according to any one of [9] to [11].

[13] The immunochromatographic apparatus according to [12], wherein the determination window of the cassette is located at a position corresponding to the first site as the detection site of the test strip, the first through hole of the cassette is located at a position corresponding to addition site of the specimen liquid in the second site of the test strip, and the second through hole of the cassette is located at a position corresponding to the addition site of the specimen liquid or developer in the third site of the test strip.

Advantageous Effects of Invention

The test strip, the cassette, and the immunochromatographic apparatus according to the present invention make it possible to shorten the measurement time as compared with the conventional method in a state of maintaining highly sensitive detection performance in the immunochromatographic measurement. In particular, they are of high utility value in the field of clinical tests.

DESCRIPTION OF EMBODIMENTS

Hereinafter, embodiments of the present invention will be described with reference to the drawings. The drawings are used for describing the present invention, and the technical scope of the present invention is not limited to the embodiments shown in the drawings.

Figure 1:
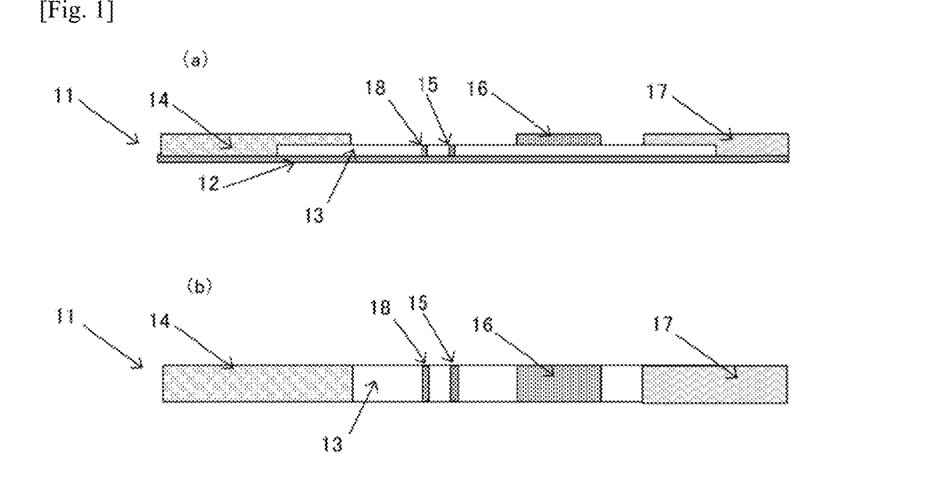
FIG. 1(a) is a side view of a test strip according to an embodiment of the present invention.
FIG. 1(b) is a plan view of the test strip according to the embodiment of the present invention.

FIG. 1 shows an example of a test strip according to the present invention. The test strip (11) is formed from a pressure sensitive adhesive sheet (12), a carrier (13), a water absorber (14), a first site (15), a second site (16), a third site (17), and a control line (18).

The first site (15) is a detection site for visually or mechanically observing measurement results, in which a first antibody capable of specifically binding to a substance to be measured is immobilized on a carrier (13) composed of a porous carrier. As the carrier (13), a nitrocellulose membrane filter is preferably used, but other cellulose membrane filters, nylon membrane filters and the like can also be used as long as they can develop a specimen liquid or developer and immobilize antibodies.

The second site (16) is a pad composed of a porous carrier containing a labeled second antibody capable of specifically binding to the substance to be measured in a specimen (hereinafter, referred to as labeled second antibody), which is a specimen liquid addition site. Compared to a site containing the labeled second antibody, the specimen liquid addition site is preferably located in a side farther from the first site (15), which is the detection site. That is, the labeled second antibody is contained in a site, close to the first site (15), of the second site (16), and the side of the second site (16) farther from the first site (15) is preferably defined as the specimen liquid addition site. Further, the vicinity of the second site (16) on the side the opposite to the first site (15) may also be defined as the specimen liquid addition site, and the form in which the second site (16) is the specimen liquid addition site also encompasses such an embodiment. According to such a configuration, the labeled second antibody easily moves in a direction of the first site (15), which is the detection site, upon addition of the specimen liquid, thereby making it possible to prevent the movement of the labeled second antibody in the opposite direction and to prevent the labeled second antibody and binding the colored microparticle which will be described later from forming a conjugate first. Therefore, good results can be obtained when, compared to specimen liquid addition site, the site containing the labeled second antibody is located generally closer to the first site (15).

The second site (16) is fixed to the carrier (13) via a double-sided tape or the like. At that time, in order that the specimen liquid added dropwise to the second site (16) can be moved to the carrier (13), a part of the second site (16) is brought into direct contact with the carrier (13). The porous carrier at the second site (16) preferably has properties of easily absorbing the specimen liquid added from the top, retaining water at a low level, and hardly absorbing the liquid moving and developing in the carrier (13). A glass fiber, a polyester film, a nonwoven fabric or the like can be used.

The specimen liquid is a liquid containing the substance to be measured, and is a biological specimen, a diluent or extract of the biological specimen, or the like. Examples of the biological specimen include whole blood, serum, plasma, urine, saliva, cerebrospinal fluid, amniotic fluid, nasal discharge, sputum, tissue exudates, nasal or throat swabs, cells and feces. The diluent or extract is a solution containing a buffer and the like, and may appropriately contain a salt, a surfactant, a protein, a saccharide, a polymer, a preservative and the like. The substance to be measured may be any substance that can be subjected to an immunoassay through an antigen-antibody reaction, including proteins, viruses, bacteria, hormones and the like.

The label substance of the labeled second antibody at the second site (16) may be any substance as long as it can prepare a substance that can specifically bind to the label substance and can be carried on the colored microparticle which will be described below. For example, haptens, biotins, peptides, proteins and the like are used as the label substance. As an example in which a hapten is used as the label substance, there can be used a combination of labeling the second antibody with N-succinimidyl 6-(2,4-dinitroanilino)hexanoate, and binding an anti-dinitrophenyl antibody, as a substance specifically binding to the label substance of the second antibody, to the colored microparticle. When a biotin is used as the label substance, there can be used a combination of labeling the second antibody with an N-hydroxysuccinimide ester derivative of a biotin (for example, trade name: EZ-Link™ NHS-LC-LC-Biotin), and binding streptavidin, as a substance specifically binding to the label substance of the second antibody, to the colored microparticles. Among these, it is preferable to use biotin as the label substance.

The porous carrier containing the labeled second antibody at the second site may be entirely or partially covered with a pad composed of a porous carrier not containing the labeled second antibody on its upper or lower surface. If necessary, the pad may contain a hydrophilic polymer, a protein, a buffer component, a surfactant, and the like. This pad preferably has properties of easily absorbing the specimen liquid, retaining water at a low level, and hardly absorbing the liquid moving and developing in the carrier (13). A glass fiber, a polyester film, a nonwoven fabric or the like can be used. Further, the second site (16) may be a part of the carrier (13) as it is, without forming an independent structure.

The third site (17) is a pad composed of a porous carrier containing colored microparticles (hereinafter, referred to as binding the colored microparticle) bound with a binding substance specifically binding to the label substance of the labeled second antibody, which is a specimen liquid or developer addition site. The specimen liquid or developer addition site is preferably located on a side farther from the first site (15), which is the detection site, than the site containing the binding colored microparticles. At the third site (17), the binding colored microparticles may be contained in a site close to the first site (15), and the vicinity thereof on the side opposite to the first site (15) may be defined as the specimen liquid or developer addition site. The form in which the third site (17) is the specimen liquid or developer addition site also encompasses such an embodiment. According to such a configuration, the binding colored microparticles easily move in the direction of the first site (15), which is the detection site, upon addition of the specimen liquid or developer. The third site (17) is fixed by the pressure sensitive adhesive sheet (12) so as to be in contact with the carrier (13), but it is also possible to extend an end of the carrier (13) (even to the right side of the third site in FIG. 1) to directly fix the third site (17) to the carrier (13). Further, the third site (17) may be a part of the carrier (13) as it is without forming an independent structure.

As the porous carrier at the third site (17), a nonwoven fabric, a glass fiber, a polyester film, or the like is used. At the third site (17), an excess specimen liquid may be added as it is, or a developer may be used instead of the specimen liquid. The developer is a solution containing a buffer and the like, and may appropriately contain a salt, a surfactant, a protein, a saccharide, a water-soluble polymer, a preservative and the like. The porous carrier containing the binding colored microparticle may be entirely or partially covered with a pad composed of another porous carrier not containing the binding colored microparticles. The pad may contain a hydrophilic polymer, a protein, a buffer component, a surfactant, and the like, if necessary. The pad preferably has a property of easily absorbing the specimen liquid or developer. A glass fiber, a polyester film, a nonwoven fabric or the like can be used.

The colored microparticle used as the binding colored microparticle at the third site (17) may be any colored microparticles usually used in the immunochromatographic method, including colloidal metals, colored latex and colored cellulose microparticle. The substance to be bound to the colored microparticle is appropriately selected depending on the label substance of the labeled second antibody, and includes antibodies thereto when the label substance is a synthetic peptide, and streptavidin, neutravidin and anti-biotin antibodies when the label substance is a biotin. Among them, it is preferable to use a biotin as the label substance of the labeled second antibody and to use streptavidin as the substance to be bound to the colored microparticles. When streptavidin is used as described above, it is preferable to form a complex with a protein in order to increase the reactivity with the biotin. Examples of the protein used in the complex include BSA and IgG. The complex can be prepared, for example, by introducing a thiol group into a protein with S-acetylmercaptosuccinic anhydride, introducing a maleimide group into streptavidin with N-[(4-maleimidomethyl)cyclohexylcarbonyloxy]sulfosuccinimide, and reacting the two products.

Here, the amount of the substance to be bound to the colored microparticle may be any amount as long as the substance can be reacted with the label substance of the labeled second antibody captured at the first site, but the maximum amount of the substance that can be bound to the colored microparticle is preferably bound in order to further increase the reactivity. The maximum amount is determined depending on the surface area of the colored microparticles, the size of the substance to be bound and the like, but can be easily set by those skilled in the art through experiments and the like.

The amount of the specimen liquid to be added to the second site and the amount of the specimen liquid or developer to be added to the third site are set depending on the size of the pad used at each site, the water content, and the like. If the amount is too small, the liquid cannot move from each site to the carrier (13). Therefore, the amount of the liquid that can move from each site to the carrier (13) is set to the minimum liquid amount, and the amount of the added liquid that is uniformly filled in the pad constituting each site is set to the maximum liquid amount. Within the range of the liquid amount, an optimal amount can be appropriately set depending on the required measurement sensitivity and the like. At least, the specimen liquid or developer to be added to the third site needs to move from the second site (16) to the first site (15), and the required liquid amount increases since the liquid moves and develops at a long distance.

The control line (18) is provided in the vicinity of the first site (15) on the side opposite to the second site (16). The control line (18) is a site where the binding colored microparticle, which have moved and developed from the third site (17) and passed through the first site (15) without having been captured there, are captured, the site indicating that the reaction has thus been performed normally. The substance forming the control line may be any substance as long as the binding colored microparticle can develop a color as a line when the specimen liquid or developer added to the third site passes through the first site. For example, as the substance to be immobilized at a position of the control line, the labeled second antibody or label substance thereof may be used. If the substance to be bound to the binding colored microparticle is streptavidin or neutravidin, a biotin may also be used. If the labeled second antibody is a mouse-derived IgG antibody, an anti-mouse IgG antibody can also be immobilized.

Further, on the side of the first site (15) and the control line (18), opposite to the second site (16), an extended portion of the carrier (13) and/or a water absorber (14) are/is provided. This makes it easier for the specimen liquid at the second site (16) to easily move toward the first site (15) and further beyond the first site (15) and develop, and, along with this, the movement and development of the specimen liquid or developer at the third site (17) toward the direction of the first site (15) become smooth. As the water absorber (14), a porous carrier having water absorption and water retention is preferable, and a cellulose film, a filter paper, a nonwoven fabric or the like is used.

The test strip of the present invention will be described in more detail. The measurement is started by adding the specimen liquid to the second site (16) and, simultaneously or immediately thereafter, adding the specimen liquid or developer to the third site (17). Here, it is preferable that the specimen liquid or developer be added to the second site (16) and the third site (17), respectively, always at the same timing as much as possible. The specimen liquid added to the second site (16) moves to the carrier (13) while dissolving the labeled second antibody retained at the second site and reacting with the substance to be measured, and develops through the carrier (13) toward the first site (15) and the third site (17). Here, as described above, the reaction product between the labeled second antibody and the substance to be measured preferably does not move toward the third site (17). Then, the specimen liquid or developer added to the third site (17) develops to the carrier (13) while dispersing the binding colored microparticle, and collides with the specimen liquid having developed from the second site (16). Due to this collision, all of the specimen liquid at the second site (16) moves and develops toward the direction of the first site (15), and the conjugate of the substance to be measured and the labeled second antibody is captured by the antibody at the first site. In a state in which the specimen liquid at the second site (16) is continuously moving to the carrier (13), the development of the liquid having moved from the third site (17) becomes very slow or is almost stopped. Then, at the stage when the specimen liquid at the second site (16) has almost all moved in the direction of the first site, the liquid having moved from the third site (17) starts to move and develop at a normal speed in the direction of the first site, so that the binding colored microparticle are captured by the label substance of the labeled second antibody bound to the substance to be measured captured by the first antibody at the first site, and color development is confirmed. Further, an excess specimen liquid or developer moves toward the extended portion of the carrier (13) and/or the water absorber (14), functions as a washing solution for the first site, and has an action of making vivid color development and stopping the reaction.

Further, in the test strip of a preferred embodiment of the present invention, the reaction between the substance to be measured and the labeled second antibody at the second site (16) and its vicinity, and the reaction between the conjugate of the substance to be measured and the labeled second antibody and the immobilized antibody at the first site (15) are performed in the absence of colored microparticle. So, the reactions can be performed efficiently without a deterioration in reactivity due to steric hindrance as in the general immunochromatographic method. In the test strips of some embodiments of the present invention, the labeled second antibody or the conjugate of the substance to be measured and the labeled second antibody may bind to the binding colored microparticle first. However, there is no problem because such a conjugate is formed in a small amount, and most of the labeled second antibody or the conjugate of the substance to be measured and the labeled second antibody moves to the first site (15) first. Further, the reaction between the label substance of the labeled second antibody and the binding colored microparticle captured via the substance to be measured at the first site is performed in a state where the binding substance is bound to the colored microparticle, and the binding colored microparticle of the present invention can react very efficiently. In the general immunochromatographic method, when the concentration of the substance to be measured is high, a large amount of the substance to be measured binds to the colored microparticle, so that the colored microparticle have high reactivity with the antibody at the first site. Since the amount of the substance to be measured that binds to the colored microparticle is reduced when the concentration is low, the colored microparticle have low reactivity with the antibody at the first site. On the other hand, in the present invention, since the colored microparticle already carry the maximum amount of the binding substance to be reacted with the label substance of the labeled second antibody, which can be bound to the colored microparticle. Therefore, even when the reaction takes place in the state in which the binding substance is bound to the colored microparticle, the colored microparticle have high reactivity with the label substance of the labeled second antibody captured at the first site, regardless of the concentration of the substance to be measured. Therefore, the reaction can be performed efficiently in a short time regardless of the concentration of the substance to be measured, and high-sensitivity measurement equal to or higher than that of the general immunochromatographic method is possible at the time when the colored microparticles pass through the first site and the background generally becomes white, that is, in a measurement time of 3 to 5 minutes regardless of the concentration of the substance to be measured. Furthermore, at this time, all the labeled second antibodies having developed from the second site have passed through the first site and the antigen-antibody reaction does not proceed any more, resulting in an advantage that no false positive appears even after a lapse of the measurement time.

Figure 2:
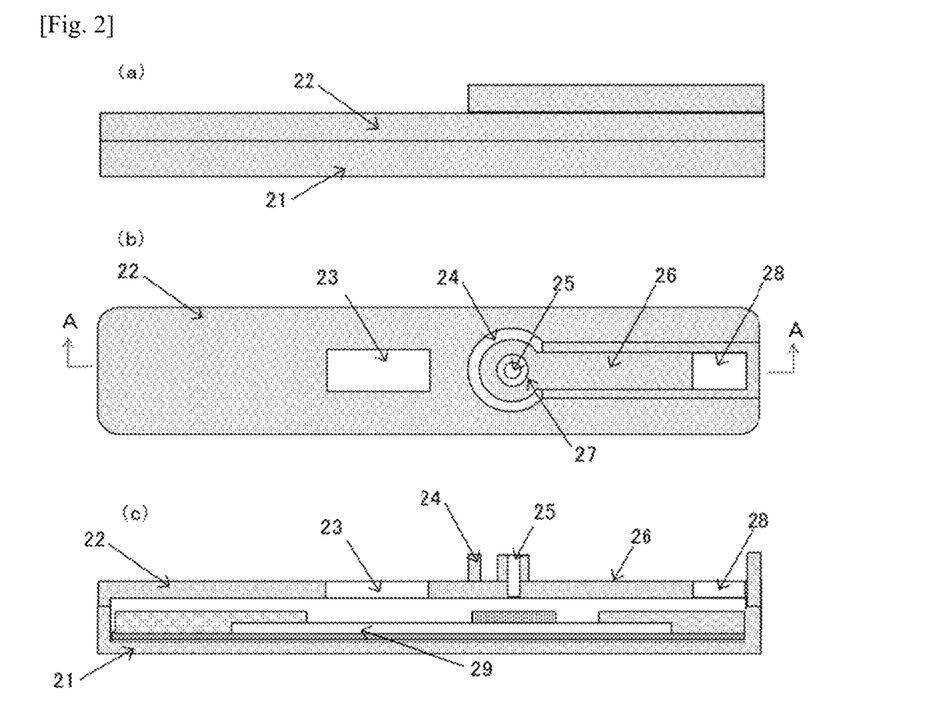
FIG. 2(a) is a side view of a cassette according to an embodiment of the present invention.
FIG. 2(b) is a plan view of the cassette according to the embodiment of the present invention.
FIG. 2(c) is a sectional view taken along line A-A of the cassette shown in FIG. 2(a).

FIG. 2 shows an example of a cassette of the present invention. The cassette of the present embodiment is a cassette for housing an immunochromatographic test strip (29) for use in the measurement of a substance to be measured contained in a specimen, here, a cassette for housing especially the test strip (29) of the present invention, and is composed of a cover (22) that covers an inspection surface of the test strip (29) and a base (21) on which the test strip (29) is placed. The material for the cassette is not particularly limited, but is formed of a resin such as plastic. The cover (22) is detachable to house the test strip (29).

The cassette of the present invention is provided with a determination window (23) which is an opening for observing the measurement result of the test strip (29) housed therein, and the measurement result can be visually or mechanically observed. Further, the cassette is provided with a specimen addition section (24) and a second through hole (28) for introducing the specimen liquid into the test strip (29) housed therein, and the specimen addition section and the second through hole are connected by a groove (26). The specimen addition section (24) is formed in a concave shape, and further has a convex part (27) on its bottom surface. The concave shape is not particularly limited, but is preferably a columnar or mortar-like shape or a combination thereof, and the bottom surface has a shape and a size capable of receiving all the dropwise added specimens, and preferably has a structure, for example, including an inclination toward the groove (26) so that the liquid easily moves to the groove (26).

The convex part (27) provided on the bottom surface of the specimen addition section (24) is a protrusion smaller than the area of the concave bottom surface when the specimen addition section (24) is viewed from above, and the shape of the convex part (27) is not particularly limited, but is preferably formed in a columnar shape. Further, the convex part (27) is provided with a first through hole (25) for introducing the dropwise added specimen liquid into the test strip (29) that is housed inside, and the diameter or width of the through hole is formed so as to be smaller than the diameter of one drop of the specimen liquid. The height of the convex part (27) and the diameter or width of the first through hole (25) are set based on the amount of the liquid desired to pass through the first through hole (25), and determined in consideration of the size of water drops, number of drops, and the width of the test strip (29) to be housed. When the width of the test strip (29) is 3 to 5 mm, the height is preferably 0.1 to 5 mm, and the diameter or width is preferably 0.5 to 3 mm.

The second through hole (28) is provided on the side opposite to the determination window when viewed from the specimen addition section (24), and is connected to the specimen addition section (24) via the groove (26) so that the specimen liquid can move. The size of the second through hole (28) is not particularly limited, but is determined in consideration of the width of the test strip (29) housed inside. For example, if the width of the test strip (29) is a normal width of about 4 mm, the width of the second through hole (28) is preferably aligned with the test strip (29). The second through hole (28) is preferably a rectangular through hole having a length of about 4 to 8 mm in the direction of the test strip (29).

The groove (26) is intended for moving the specimen that has not entered the first through hole (25) toward the second through hole (28), and the specimen can be moved by capillarity, gradient, etc. It is preferable to install a water-absorbing porous carrier made of a nonwoven fabric, a filter paper, a glass fiber or the like in the groove (26), in which case the water-absorbing porous carrier is preferably installed so that one end of the carrier is in contact with the specimen addition section (24), and that the other end thereof is in contact with the test strip (29) housed inside through the second through hole (28). A lid is preferably attached to the groove (26) to fix the water-absorbing porous carrier. On the inside of the lid, a protrusion for fixing the water-absorbing porous carrier and a protrusion for bringing the test strip (29) housed inside into contact with the water-absorbing porous carrier through the second through hole (28) are preferably formed. Further, the lid may form a part of the concave shape of the specimen addition section (24).

Figure 3:
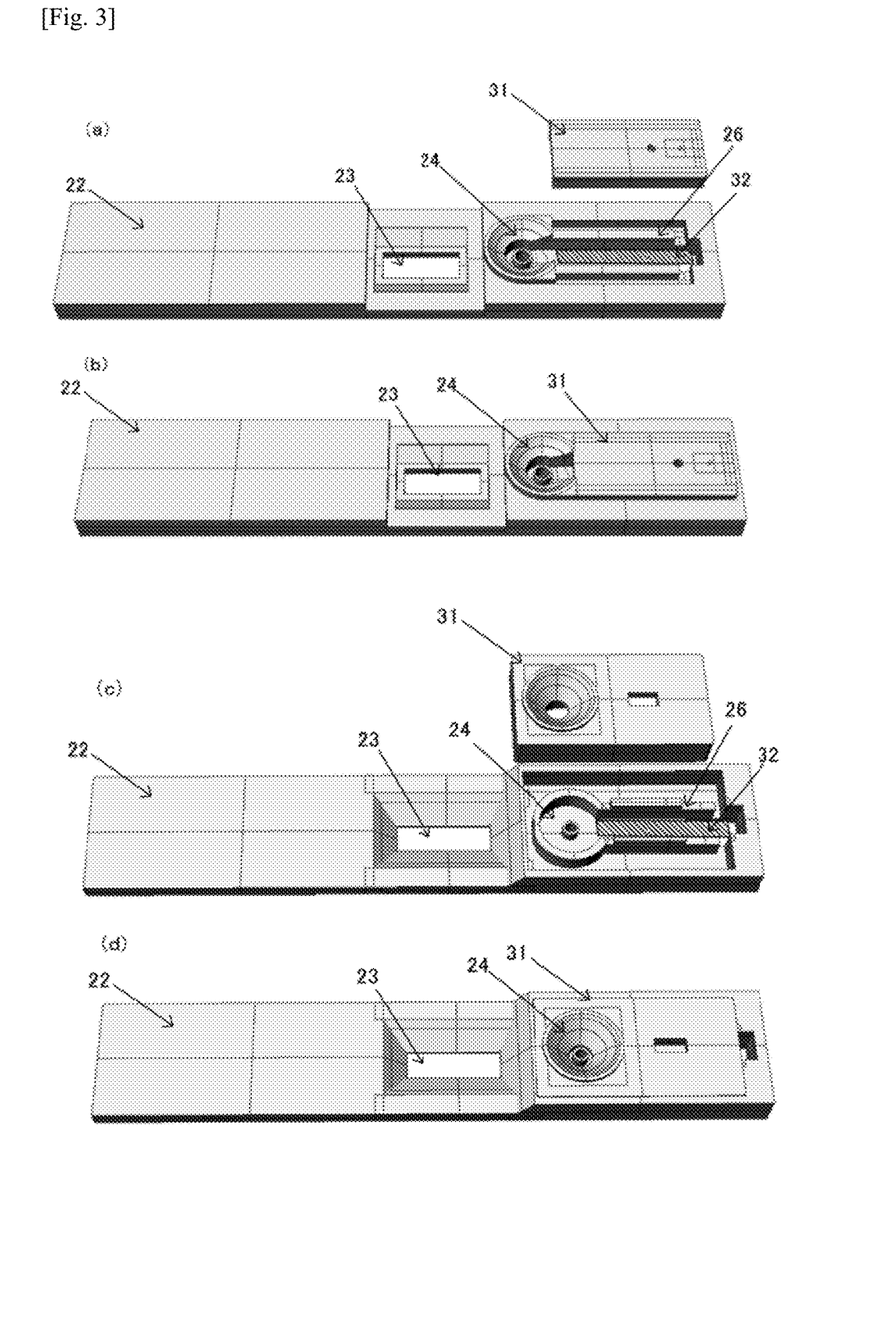
FIG. 3(a) is a perspective view showing the cassette according to the embodiment of the present invention, in a state where a lid of a groove is removed.
FIG. 3(b) is a perspective view of the cassette in FIG. 3(a) when the lid of the groove is attached.
FIG. 3(c) is a perspective view showing the cassette according to the embodiment of the present invention in which the lid of the groove is formed integrally with a specimen addition section, in a state where the lid is removed.
FIG. 3(d) is a perspective view of the cassette in FIG. 3(c) when the lid of the groove is attached.

FIG. 3 shows an example in which a lid is attached. FIGS. 3(a) and 3(b) show an example in which a water-absorbing porous carrier (32) is attached to the groove (26) and a lid (31) covers only the groove (26), in which (a) shows a state in which the lid (31) is removed and (b) shows a state in which the lid (31) is attached. On the other hand, FIGS. 3(c) and 3(d) show an example in which the water-absorbing porous carrier (32) is attached, the lid (31) covers the groove (26), and is formed integrally as a part of the concave shape of the specimen addition section (24), in which (c) shows a state in which the lid (31) is removed, and (d) shows a state in which the lid (31) is attached.

An exemplary case where the cassette of the present invention and the test strip of the present invention are used in combination will be described in more detail. The positional relationship between each site of the cassette of the present invention and the test strip of the present invention is such that the determination window of the cassette is provided so that the first site or the first site and the control line of the test strip can be confirmed, that the first through hole of the cassette is provided at a position corresponding to the specimen liquid addition site at the second site of the test strip, and further that the second through hole of the cassette is provided at a position corresponding to the specimen liquid or developer addition site at the third site of the test strip. Further, protrusions for bringing the carrier and the water absorber, the carrier and the second site, and the carrier and the third site in the test strip into close contact with each other are preferably provided on the inner surface of the cover (22). Preferably, a protrusion is also provided at an outlet of the first through hole.

The measurement is started by dropwise adding the specimen liquid to the specimen addition section. A part of the specimen liquid dropwise added to the specimen addition section moves from the first through hole of the convex part to the specimen liquid addition site at the second site of the test strip, and the remaining specimen liquid that could not pass through the first through hole moves from the second through hole via the groove to the specimen liquid or developer addition site at the third site of the test strip, so that predetermined reactions can proceed. The amount of the specimen liquid to be used in the measurement is set depending on the sizes of the pads used at the second site and the third site, the water content, etc. For example, when the test strip has a width of about 3 to 5 mm and a length of about 70 to 80 mm, and the amount of one drop of the liquid is about 15 to 30 µL, 2 to 5 drops are preferable.

An immunochromatographic apparatus of the present invention can be prepared by housing the test strip of the present invention in the cassette of the present invention. The measurement is performed in this manner, so that the test strip of the present invention which required dropwise addition of the specimen liquid to two places can be implemented through an operation of dropwise adding the specimen to one place as in the conventional immunochromatographic method. Furthermore, when the specimen liquid or developer is added dropwise to two places, the reproducibility of the measurement may be reduced unless the time and interval of dropwise adding the specimen liquid or developer to the two places are constant. However, when the cassette or immunochromatographic apparatus of the present invention is used, the time and interval of supplying the specimen liquid or developer to two places are determined based, for example, on the length of the groove, the length of the water-absorbing porous carrier installed in the groove, and the water absorption rate, without any variation in operation technique. Therefore, the effect of improving the measurement reproducibility can be obtained.

The cassette of the present invention can be suitably applied not only to the test strip of the present invention, but also to test strips of types in which the specimen liquid or developer is added dropwise to two places. Examples of such test strips include the test strip described in JP 2001-337091 A, the test strip described in JP H10-300750 A, and the test strip described in JP 2009-002822 A. Also in these, the same effects as those obtained by the combination of the cassette of the present invention and the test strip of the present invention can be obtained.

The specimen used in the measurement can be an extracted specimen obtained by extracting a biological specimen collected from whole blood, serum, plasma, urine, nasal cavity or pharynx with a test solution, and, besides, serum, plasma or urine can be used as a measurement specimen as it is. It is preferable to use whole blood diluted with a test solution such as an isotonic solution, and to filter it through a filter or mount a blood cell separation membrane at the second and third sites of the test strip, in order to remove blood cell components from the diluted solution. The substance to be measured may be any substance that can be subjected to an immunoassay through an antigen-antibody reaction, including proteins, viruses, bacteria, hormones and the like.

EXAMPLES

Hereinafter, the present invention will be described based on examples, but is not limited thereto.

Examples (1) Preparation of Test Strip for Measurement of Influenza Virus
1. Preparation of Biotin-Labeled Anti-Influenza A Antibody
   To 1 mL of 2.5 mg/mL anti-influenza virus A mouse monoclonal antibody (manufactured by Meridian, product number C1733M), 15 µL of 6 mg/mL sulfo-NHS-LC-LC-biotin (manufactured by Thermo Fisher Scientific) was added to cause a reaction at room temperature for 30 minutes.

2. Preparation of BSA-Streptavidin Complex

To 1 mL of 5 mg/mL bovine serum albumin (BSA), 50 µL of 60 mg/mL S-acetylmercaptosuccinic anhydride solution was added to cause a reaction at room temperature for 30 minutes. Next, 1 mL of 36 mg/mL hydroxylamine hydrochloride was added to the reaction product to cause a reaction at room temperature for 10 minutes, and the reaction product was replaced with a 0.1 M phosphate buffer (pH 6.0) to obtain thiolated (SH-modified) BSA.

To 1 mL of 5 mg/mL streptavidin, N-[(4-maleimidomethyl)cyclohexylcarbonyloxy]sulfosuccinimide (manufactured by Thermo Fisher Scientific) was added to cause a reaction at room temperature for 1 hour, and the reaction product was replaced with 0.1 M phosphate buffer (pH 6.0) to obtain maleimidated streptavidin.

An equimolar mixture of thiolated (SH-modified) BSA and maleimidated streptavidin were mixed to cause a reaction at room temperature for 1 hour, thereby preparing a BSA-streptavidin complex.

3. Preparation of Colloidal Gold-Labeled Streptavidin

To 3 mL of a colloidal gold suspension (manufactured by Tanaka Kikinzoku Kogyo K.K.), 10 µL of the 2.5 mg/mL BSA-streptavidin complex prepared in 2 was added to cause a reaction at room temperature for 30 minutes. Next, 3 mL of 5 mg/mL BSA was added to cause a reaction at room temperature for 30 minutes. The colloidal gold was washed by centrifugation, and suspended in 0.3 mL of 10 mM Tris buffer (pH 8.0).

4. Preparation of Anti-Influenza Antibody-Immobilized Carrier

Anti-influenza virus A mouse monoclonal antibody (manufactured by Meridian, product No. C1736M) (1 mg/mL) was applied to a nitrocellulose membrane (45 mm×150 mm, Millipore), in a line shape at a position 22 mm distant from the lower end of the nitrocellulose membrane under the condition of 1 µL/cm. After the application, the coating was dried at 40° C. for 30 minutes, impregnated with a 0.5% casein solution, and then dried at 40° C. for 1 hour to prepare an anti-influenza antibody-immobilized carrier.

5. Preparation of Biotin-Labeled Antibody-Containing Pad

1 µL of the 2.5 mg/mL biotin-labeled anti-influenza A antibody prepared in 1 was added to 300 µL of 2% trehalose-containing 10 mM Tris buffer (pH 8.0). This solution was impregnated into a glass fiber sheet (11 mm×150 mm, manufactured by Millipore), followed by freeze-drying.

6. Preparation of Colloidal Gold-Labeled Streptavidin-Containing Pad

The colloidal gold-labeled streptavidin suspension (0.23 mL) prepared in 3 was impregnated into a glass fiber sheet (5 mm×150 mm, manufactured by Millipore), followed by freeze-drying.

7. Preparation of Immunochromatographic Test Strip

An anti-influenza antibody-immobilized carrier was bonded from a position 11 mm distant from the lower end of a pressure sensitive adhesive sheet (80 mm×150 mm), and a cellulose fiber pad (35 mm×150 mm) was bonded thereto from the upper end of the pressure sensitive adhesive sheet. Next, a colloidal gold-labeled streptavidin-containing pad was applied from a position 7 mm distant from the lower end of the pressure sensitive adhesive sheet so as to partially overlap the anti-influenza antibody-immobilized carrier, and then a nonwoven fabric (8 mm×150 mm) was bonded thereto from the lower end of the pressure sensitive adhesive sheet. Furthermore, a 10 mm-wide double-sided tape was applied from a position 16 mm distant from the lower end of the pressure sensitive adhesive sheet toward the upper end side. A biotin-labeled antibody-containing pad was bonded from a position 17 mm distant from the lower end of the pressure sensitive adhesive sheet toward the upper end side, and cut into 4 mm width to prepare an immunochromatographic test strip.

8. Preparation of Immunochromatographic Apparatus

A cassette was prepared in which, at a position 23 mm distant from the lower end position when the test strip was prepared in 7 was housed, a first through hole having a diameter of 1.6 mm was provided in a convex part having a diameter of 3 mm×a height of 2 mm, further, a 4 mm×6 mm second through hole was provided based on the position of the lower end, and a 20 mm×4 mm nonwoven fabric was installed in a groove. The test strip prepared in 7 was housed in this cassette to prepare an immunochromatographic apparatus for measuring influenza A virus.

(2) Specimen Preparation and Measurement

A diluted specimen of the influenza A antigen solution (manufactured by Fizgerald) was prepared using 50 mM Tris buffer (pH 8.5) containing 0.5% Triton-X100 (registered trademark). Table 1 shows the dilution factors of the diluted specimens. The prepared diluent was placed in an eye dropper, and three drops thereof were added to the convex part of the specimen addition section of the cassette to start the reaction. The time lapse from the start of the reaction to the determination that the result was positive or negative and the detection sensitivity were examined.

The following comparative examples all use a general immunochromatographic method as measurement principle, and a conjugate of a first antibody in which colored microparticle and an anti-influenza virus antibody were bound to each other and influenza virus in the specimen liquid was bound to an immobilized anti-influenza virus second antibody for detection.

Comparative Example 1

As Comparative Example 1, a commercially available influenza virus antigen detection reagent ImunoAce Flu (registered trademark) was used. The diluted specimen was prepared in the same manner as in the Example using the extract attached to the kit. The reaction was started by adding three drops of the diluted specimen, and the time lapse from the start of the reaction to the determination that the result was positive or negative and the detection sensitivity were examined.

Comparative Example 2

As Comparative Example 2, a test was conducted in the same manner as in Comparative Example 1, using a commercially available influenza virus antigen detection reagent Finevision Influenza (registered trademark).

Comparative Example 3

As Comparative Example 3, a test was conducted in the same manner as in Comparative Example 1, using a commercially available influenza virus antigen detection reagent Alsonic (registered trademark).

Evaluation Result

Table 1 shows the results of the Example and the Comparative Examples.

The presence or absence of a detection line with the lapse of time after the start of the reaction was visually confirmed. When a line was confirmed even slightly, the result was determined to be "+". When no line was confirmed, the result was determined to be "−". In the table, the determinations put in parentheses are those when the time exceeds the time specified by the commercial kit in each comparative example.

At 4000-fold dilution, the result was determined to be "+" in 3 to 4 minutes in all the examples, and the results did not change even if the reaction time was extended to 15 minutes.

At 8000-fold dilution, the result was determined to be "+" in 3 minutes in the Example, whereas it took 5 minutes in Comparative Example 1 and 4 minutes in Comparative Example 3, until the result was determined to be "+". Further, the result was determined to be "−" in Comparative Example 2, indicating that the present invention has high sensitivity. Further, in Comparative Example 2, the result was determined to be "+" in 8 minutes that exceeded the determination time specified by the kit.

At 16000-fold dilution, the result was determined to be "−" in 3 minutes in the Example, and the determination did not change even if the reaction time was extended to 15 minutes. In the Comparative Examples, the results were all determined to be "−" in the determination time specified by the kit, but a phenomenon that the result was determined to be "+" was observed when the determination time exceeded the specified determination time.

A comparison between the Example of the present invention and the Comparative Examples using the conventional immunochromatographic method as measurement principle, based on these results, revealed that the present invention is excellent in the following respects.

Regarding the measurement sensitivity, when the 8000-fold diluted specimen was measured, the line appeared faster in the present invention than in the Comparative Examples, which verified that the present invention had higher measurement sensitivity than each of the Comparative Examples. Further, in the Comparative Examples, the line appearance time was delayed when the dilution factor of the specimen became greater, whereas the line appearance time was the same regardless of the dilution factor in the present invention. This is a result demonstrating the superiority that the present invention enables high-sensitivity detection in a short time regardless of the concentration of the substance to be measured in the specimen, and it can be said that the claimed apparatus is highly useful in clinical test sites.

Next, in order to confirm the stability of the determination result, when the result obtained in the specified determination time was compared with the result obtained after a lapse of 15 minutes from the specified determination time, the determination result was not changed in the present invention, but was changed in each of the Comparative Examples. In the methods of the comparative examples, the reaction is continued even after a lapse of the determination time, and thus the resultant sensitivity becomes higher when the reaction time is longer, but the determination time becomes longer accordingly, leading to reduction in convenience. Further, when the reaction time is longer, a line may appear due to a non-specific reaction depending on the type of specimen, so a reaction time of about 5 to 10 minutes is set from the overall performance. Therefore, each of the Comparative Examples involves a problem that an incorrect determination may be made if the measurer does not strictly observe the reaction time, whereas such a phenomenon does not occur in the present invention, so that strict time management becomes unnecessary. Thus, the claimed method has been proved to be excellent in convenience when used in actual clinical sites.

TABLE 1

|  | Dilution factor | Reaction time | | | | | |
|---|---|---|---|---|---|---|---|
|  |  | 3 min. | 4 min. | 5 min. | 8 min. | 10 min. | 15 min. |
| Examples | 4000 fold | + | + | + | + | + | + |
|  | 8000 fold | + | + | + | + | + | + |
|  | 16000 fold | − | − | − | − | − | − |
| Comparative Example 1 Specified determination time: 8 min. | 4000 fold | + | + | + | + | (+) | (+) |
|  | 8000 fold | − | − | + | + | (+) | (+) |
|  | 16000 fold | − | − | − | − | (−) | (+) |
| Comparative Example 2 Specified determination time: 5 min. | 4000 fold | − | + | + | (+) | (+) | (+) |
|  | 8000 fold | − | − | − | (+) | (+) | (+) |
|  | 16000 fold | − | − | − | (−) | (−) | (+) |
| Comparative Example 3 Specified determination time: 5 min. | 4000 fold | + | + | + | (+) | (+) | (+) |
|  | 8000 fold | − | + | + | (+) | (+) | (+) |
|  | 16000 fold | − | − | − | (−) | (+) | (+) |

REFERENCE SIGNS LIST 11, 29 Test strip
12 Pressure sensitive adhesive sheet
13 Carrier
14 Water absorber
15 First site
16 Second site
17 Third site
18 Control line
21 Base
22 Cover
23 Determination window
24 Specimen addition section
25 First through hole
26 Groove
27 Convex part
28 Second through hole
31 Lid
32 Water-absorbing porous carrier

The invention claimed is:
1. A test strip for detecting a substance to be measured in a specimen liquid by an immunochromatographic method, the test strip comprising:
(1) a first site that is a detection site, where a first antibody specifically binding to the substance to be measured is immobilized on a porous carrier;
(2) a second site that is an addition site of the specimen liquid, where a second antibody bound with a label substance specifically binding to the substance to be measured and having a recognition site different from that of the first antibody is retained on a porous carrier so as to be movable; and
(3) a third site that is an addition site of the specimen liquid or a developer, where a colored microparticle bound with a substance specifically binding to the label substance of the second antibody are retained on a porous carrier so as to be movable,
wherein the second site is provided between the first site and the third site, and the specimen liquid or developer can move, due to capillarity, from the second site to the first site and from the third site to the first site.

2. The test strip according to claim 1, further comprising a control line in the vicinity of the first site on the side opposite to the second site, the control line indicating that a reaction has been performed normally.

3. The test strip according to claim 1, wherein, in the second site, compared to the addition site of the specimen liquid, a site containing the labeled second antibody is located closer to the first site.

4. The test strip according to claim 1, further comprising a water absorber or a porous carrier for absorbing or moving the specimen liquid or developer on the side of the first site, opposite to the second site.

5. The test strip according to claim 1, wherein the label substance of the second antibody is a biotin, and the substance specifically binding to the label substance of the second antibody, which is bound to the colored microparticle, is selected from the group consisting of streptavidin, neutravidin and an anti-biotin antibody.

6. The test strip according to claim 5, wherein the streptavidin is a complex with a protein.

7. The test strip according to claim 1, wherein the colored microparticle is selected from the group consisting of a colloidal metal, a colored latex, and a colored cellulose particle.

8. An immunochromatographic apparatus, in which the test strip according to claim 1 is housed in a cassette having a determination window and a concave specimen addition section arranged on its upper surface,
the cassette having:
a convex part having a first through hole in the concave specimen addition section;
a second through hole on the side of the concave specimen addition section, opposite to the determination window; and
a groove formed in an area ranging from the concave specimen addition section to the second through hole, the groove having a flow path for sending a part of the added specimen liquid leaked from the first through hole of the convex part.

9. The immunochromatographic apparatus according to claim 8, wherein the determination window of the cassette is located at a position corresponding to the first site as the detection site of the test strip, the first through hole of the cassette is located at a position corresponding to addition site of the specimen liquid in the second site of the test strip, and the second through hole of the cassette is located at a position corresponding to the addition site of the specimen liquid or developer in the third site of the test strip.

10. The test strip according to claim 2, further comprising a water absorber or a porous carrier for absorbing or moving the specimen liquid or developer on the side of the first site and the control line, opposite to the second site.

11. The immunochromatographic apparatus according to claim 8, wherein, in the cassette, the groove is provided with a porous carrier as the flow path for sending the liquid, and wherein, in the cassette, one end of the porous carrier is provided so as to come into contact with the test strip housed in the cassette through the second through hole.

12. The immunochromatographic apparatus according to claim 8, wherein the cassette further has a lid attached to the groove.

13. A method of using the test strip according to claim 1, comprising
adding the specimen liquid to the second site and the third site simultaneously, or
adding the specimen liquid to the second site and subsequently adding the specimen liquid or the developer to the third site.

* * * * *